(12) United States Patent
Govari et al.

(10) Patent No.: US 12,290,308 B2
(45) Date of Patent: May 6, 2025

(54) HIGH FREQUENCY UNIPOLAR ELECTROPORATION ABLATION

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yuri Shamis, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 535 days.

(21) Appl. No.: 17/501,379

(22) Filed: Oct. 14, 2021

(65) Prior Publication Data

US 2023/0120856 A1 Apr. 20, 2023

(51) Int. Cl.
| | | |
|---|---|---|
| *A61B 18/12* | (2006.01) | |
| *A61B 18/00* | (2006.01) | |
| *A61B 18/14* | (2006.01) | |
| *A61B 18/16* | (2006.01) | |

(52) U.S. Cl.
CPC ...... *A61B 18/1492* (2013.01); *A61B 18/1206* (2013.01); *A61B 18/1233* (2013.01); *A61B 18/16* (2013.01); *A61B 2018/00577* (2013.01); *A61B 2018/00613* (2013.01); *A61B 2018/00773* (2013.01); *A61B 2018/124* (2013.01); *A61B 2018/1253* (2013.01); *A61B 2018/165* (2013.01); *A61B 2018/167* (2013.01)

(58) Field of Classification Search
CPC ............ A61B 18/1492; A61B 18/1206; A61B 2018/00577; A61B 2018/00613; A61B 2018/00773; A61B 2018/167; A61B 2018/1253; A61B 2034/101; A61B 2034/104
See application file for complete search history.

(56) References Cited

U.S. PATENT DOCUMENTS

| | | |
|---|---|---|
| 5,391,199 A | 2/1995 | Ben Haim |
| 6,239,724 B1 | 5/2001 | Doron |
| 6,332,089 B1 | 12/2001 | Acker |

(Continued)

FOREIGN PATENT DOCUMENTS

WO WO1996005768 A1 2/1996

OTHER PUBLICATIONS

European Search report for corresponding EPA No. 2201225.4 dated Feb. 17, 2023.

*Primary Examiner* — Ronald Hupczey, Jr.
*Assistant Examiner* — Dana Stumpfoll

(57) ABSTRACT

An electroporation ablation system includes a probe to be inserted into a body part of a living subject, and including a distal end including at least one electrode, body-surface patches to be applied to a skin surface, an ablation power generator to apply at least one first electrical pulse train between the electrode(s) and first one(s) of the body-surface patches, and a processor to provide a measurement of movement of the living subject responsively to applying the first electrical pulse train(s) between the electrode(s) and the first one(s) of the body-surface patches, and select second one(s) of the body-surface patches responsively to the measurement of movement, and wherein the ablation power generator is configured to apply at least one second electrical pulse train between the electrode(s) and the second one(s) of the body-surface patches.

20 Claims, 5 Drawing Sheets

(56) References Cited

U.S. PATENT DOCUMENTS

Figure 1:
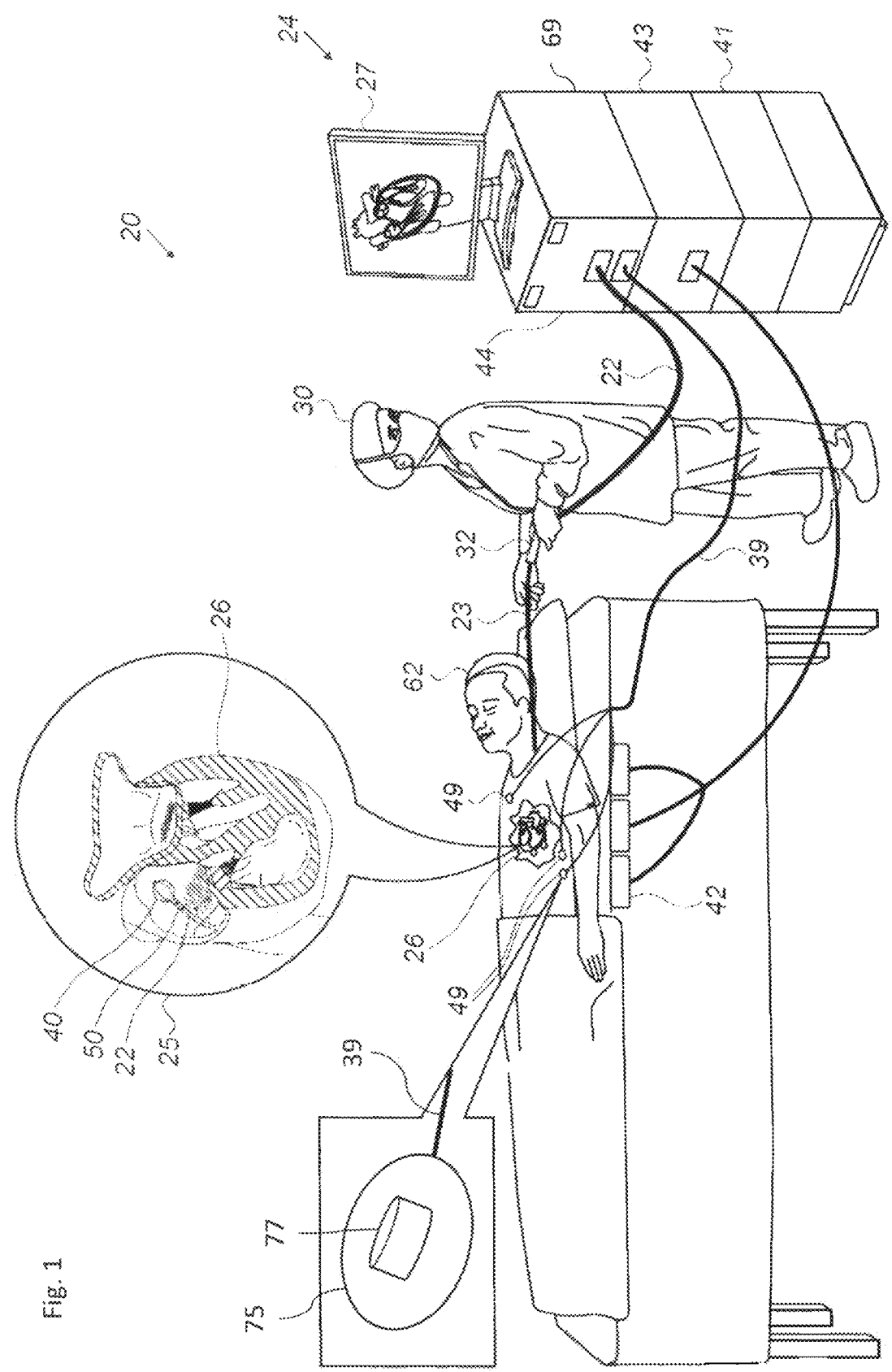

| | | |
|---|---|---|
| 6,484,118 B1 | 11/2002 | Govari |
| 6,618,612 B1 | 9/2003 | Acker |
| 6,690,963 B2 | 2/2004 | Ben Haim |
| 7,756,576 B2 | 7/2010 | Levin |
| 7,848,787 B2 | 12/2010 | Osadchy |
| 7,869,865 B2 | 1/2011 | Govari |
| 2002/0065455 A1 | 5/2002 | Ben Haim |
| 2003/0120150 A1 | 6/2003 | Govari |
| 2004/0068178 A1 | 4/2004 | Govari |
| 2008/0051777 A1* | 2/2008 | Haemmerich ..... A61B 18/1233 606/33 |
| 2015/0320481 A1* | 11/2015 | Cosman, Jr. ........... A61B 34/10 606/35 |
| 2018/0098807 A1 | 4/2018 | Schwartz |
| 2018/0296277 A1* | 10/2018 | Schwartz ........... A61B 18/1492 |
| 2019/0201091 A1* | 7/2019 | Yates ............. A61B 18/1233 |
| 2019/0223948 A1 | 7/2019 | Stewart |
| 2020/0069367 A1* | 3/2020 | Sinnott ................ A61B 18/16 |
| 2020/0077938 A1 | 3/2020 | Jung |
| 2020/0107879 A1 | 4/2020 | Stewart |
| 2021/0113265 A1 | 4/2021 | D'Agostino |
| 2021/0299456 A1 | 9/2021 | Smith |

\* cited by examiner

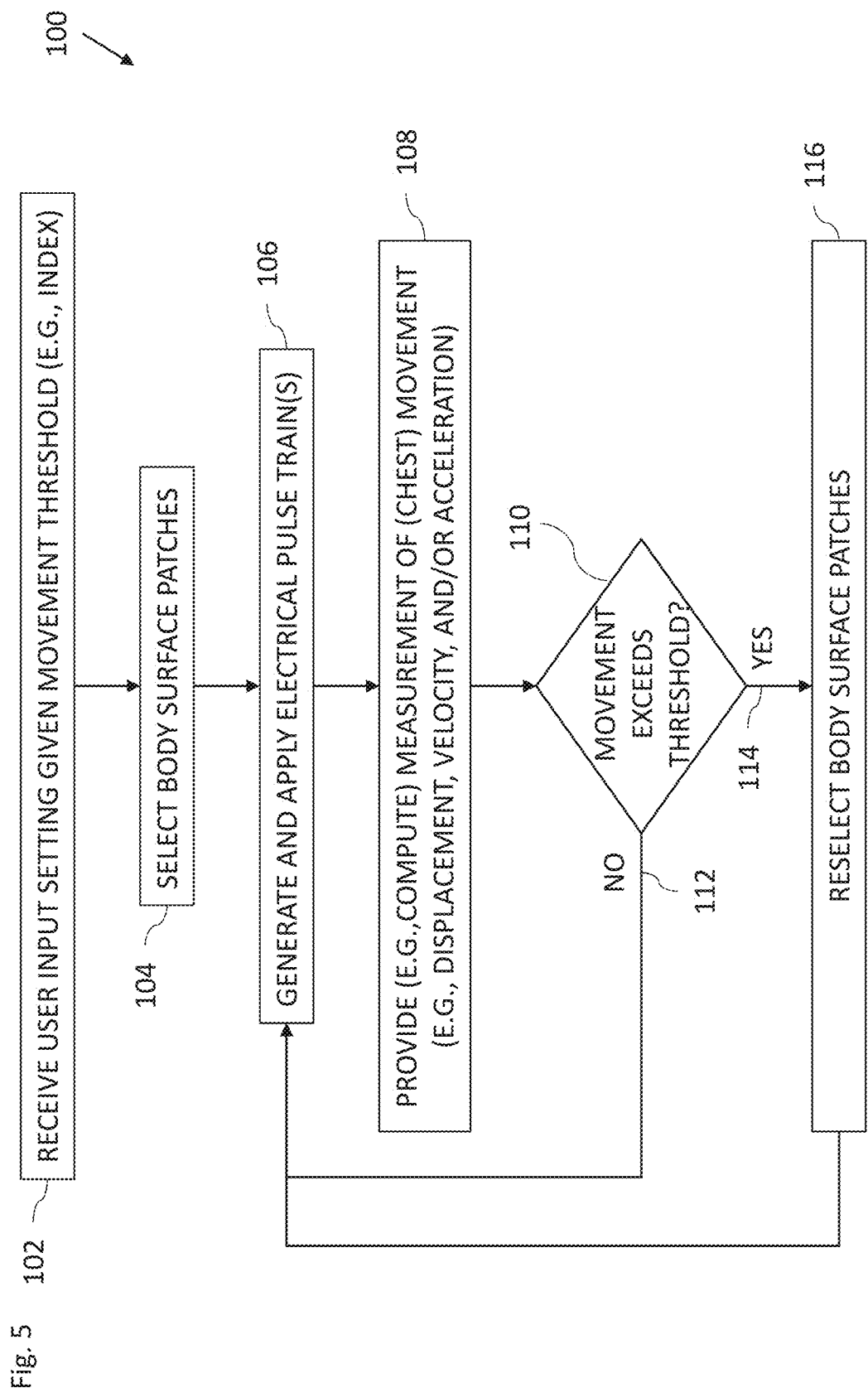

HIGH FREQUENCY UNIPOLAR ELECTROPORATION ABLATION

FIELD OF THE INVENTION

The present invention relates to medical systems, and in particular, but not exclusively to ablation systems.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include the use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied through the tip electrode(s) of the ablating catheter, and current flows through the media that surrounds it, i.e., blood and tissue, between the tip electrode(s) and an indifferent electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in the formation of a lesion within the cardiac tissue which is electrically non-conductive.

Irreversible electroporation (IRE) applies short electrical pulses that generate high enough electrical fields (typically greater than 450 Volts per centimeter) to irreversibly damage the cells. Non-thermal IRE may be used in treating different types of tumors and other unwanted tissue without causing thermal damage to surrounding tissue. Small electrodes are placed in proximity to target tissue to apply short electrical pulses. The pulses increase the resting transmembrane potential, so that nanopores form in the plasma membrane. When the electricity applied to the tissue is above the electric field threshold of the target tissue, the cells become permanently permeable from the formation of nanopores. As a result, the cells are unable to repair the damage and die due to a loss of homeostasis and the cells typically die by apoptosis.

Irreversible electroporation may be used for cardiac ablation as an alternative to other cardiac ablation techniques, e.g., radio frequency (RF) cardiac ablation. Irreversible electroporation cardiac ablation is sometimes referred to as Pulse Field Ablation (PFA). As IRE is generally a low thermal technique, IRE may reduce the risk of collateral cell damage that is present with the other techniques. e.g., in RF cardiac ablation.

SUMMARY

There is provided in accordance with an embodiment of the present invention, a electroporation ablation system, including a probe configured to be inserted into a body part of a living subject, and including a distal end comprising at least one electrode, a plurality of body-surface patches configured to be applied to a skin surface of the living subject, an ablation power generator configured to be selectively electrically connected to the at least one electrode and at least one of the body-surface patches, and configured to generate at least one first electrical pulse train, and apply the at least one first electrical pulse train between the at least one electrode and at least a first one of the body-surface patches, and a processor configured to provide a measurement of movement of the living subject responsively to applying the at least one first electrical pulse train between the at least one electrode and the at least first one of the body-surface patches, and select at least a second one of the body-surface patches responsively to the measurement of movement of the living subject, and wherein the ablation power generator is configured to generate at least one second electrical pulse train, and apply the at least one second electrical pulse train between the at least one electrode and the at least second one of the body-surface patches.

Further in accordance with an embodiment of the present invention at least a third one of the body-surface patches is configured to provide at least one position signal, and the processor is configured to provide the measurement of movement responsively to the at least one position signal.

Still further in accordance with an embodiment of the present invention, the system includes magnetic field generator coils configured to generate alternating magnetic fields in a region including the at least third one of the body-surface patches, wherein the at least third one of the body-surface patches includes at least one magnetic sensor configured to provide the at least one position signal responsively to sensing the generated alternating magnetic fields, and the processor is configured to compute the measurement of movement responsively to the at least one position signal received from the at least magnetic sensor.

Additionally in accordance with an embodiment of the present invention the at least third one of the body-surface patches includes at least one respective patch electrode configured to provide the at least one position signal, and the processor is configured to compute the measurement of movement responsively to the at least one position signal received from the at least one respective patch electrode.

Moreover, in accordance with an embodiment of the present invention the processor is configured to select the at least second one of the body-surface patches while a given ablation location of the body part is being ablated, and the ablation power generator is configured to generate the at least one first electrical pulse train and the at least one second electrical pulse train to ablate the given ablation location of the tissue of the body part.

Further in accordance with an embodiment of the present invention the ablation power generator is configured to generate the at least one first electrical pulse train to ablate a first ablation location of tissue of the body part, and the at least one second electrical pulse train to ablate a second, different, ablation location of the tissue of the body part.

Still further in accordance with an embodiment of the present invention the processor is configured to select the at least second one of the body-surface patches such that the at least second one of the body-surface patches include the at least first one of the body-surface patches and at least another one of the body-surface patches.

Additionally in accordance with an embodiment of the present invention the processor is configured to randomly select at least one of the at least second one of the body-surface patches.

Moreover, in accordance with an embodiment of the present invention the processor is configured to select the at least second one of the body-surface patches such that the at least second one of the body-surface patches are at least partially different to the at least first one of the body-surface patches.

Further in accordance with an embodiment of the present invention the processor is configured to select the at least first one of the body-surface patches to include at least one of the body-surface patches attached to a chest of the living subject, and at least one of the body-surface patches attached to a back of the living subject.

There is also provided in accordance with another embodiment of the present invention, a electroporation ablation method, including generating at least one first electrical pulse train, applying the at least one first electrical pulse train between at least one electrode of a distal end of a probe inserted into a body part of a living subject, and at least a first one of a plurality of body-surface patches applied to a skin surface of the living subject, providing a measurement of movement of the living subject responsively to applying the at least one first electrical pulse train between the at least one electrode and the at least first one of the body-surface patches, selecting at least a second one of the body-surface patches responsively to the measurement of movement of the living subject, generating at least one second electrical pulse train, and applying the at least one second electrical pulse train between the at least one electrode and the at least second one of the body-surface patches.

Still further in accordance with an embodiment of the present invention at least a third one of the body-surface patches is configured to provide at least one position signal, and the providing includes providing the measurement of movement responsively to the at least one position signal.

Additionally in accordance with an embodiment of the present invention, the method includes generating alternating magnetic fields in a region including the at least third one of the body-surface patches, at least one magnetic sensor included in the at least third one of the body-surface patches providing the at least one position signal responsively to sensing the generated alternating magnetic fields, and computing the measurement of movement responsively to the at least one position signal received from the at least magnetic sensor.

Moreover, in accordance with an embodiment of the present invention, the method includes providing the at least one position signal by at least one respective patch electrode included in the at least third one of the body-surface patches, and computing the measurement of movement responsively to the at least one position signal received from the at least one respective patch electrode.

Further in accordance with an embodiment of the present invention, the method includes selecting the at least second one of the body-surface patches while a given ablation location of the body part is being ablated, and generating the at least one first electrical pulse train and the at least one second electrical pulse train to ablate the given ablation location of the tissue of the body part.

Still further in accordance with an embodiment of the present invention the generating of the at least one first electrical pulse train is performed to ablate a first ablation location of tissue of the body part, and the generating of the at least one second electrical pulse train is performed to ablate a second, different, ablation location of the tissue of the body part.

Additionally in accordance with an embodiment of the present invention the selecting of the at least second one of the body-surface patches is performed such that the at least second one of the body-surface patches include the at least first one of the body-surface patches and at least another one of the body-surface patches.

Moreover, in accordance with an embodiment of the present invention the selecting includes randomly selecting at least one of the at least second one of the body-surface patches.

Further in accordance with an embodiment of the present invention the selecting of the at least second one of the body-surface patches is performed such that the at least second one of the body-surface patches are at least partially different to the at least first one of the body-surface patches.

Still further in accordance with an embodiment of the present invention, the method includes selecting the at least first one of the body-surface patches to include at least one of the body-surface patches attached to a chest of the living subject, and at least one of the body-surface patches attached to a back of the living subject.

DETAILED DESCRIPTION OF EXEMPLARY EMBODIMENTS

Overview

Irreversible electroporation (IRE) is generally performed by applying electrical pulse trains in a bipolar fashion between two electrodes or two sub-sets of electrodes that are in contact with tissue of a body part (e.g., a heart chamber) of a patient. When the probe inserted into the body part is a focal catheter with a single ablation electrode, the above bipolar IRE is impossible. Therefore, unipolar IRE may be performed by applying electrical pulse trains between an electrode situated in the body part and one or more body-surface patches attached to the skin of the chest and/or back and/or leg etc. of the patient.

When performing unipolar IRE, the low equivalent capacitance of the patient (about 5 nano Farads (nF)) makes regulation of the electroporation difficult, because of the associated high impedance. In bipolar IRE, i.e., between two local electrodes, the equivalent capacitance is about 50 nF. Another problem with unipolar IRE is the fact that the effect of the IRE current is distributed through the patient (in bipolar IRE, the current is localized between the two local electrodes).

Embodiments of the present invention, solve the above problems by operating an IRE ablation power generator to produce pulse trains having a high pulse frequency in a range of 0.5 megahertz (MHz) to 10 MHz, and typically about 1 MHz. The high frequency counteracts the low capacitance of the patient. However, IRE at such a high frequency is not as efficient as IRE at lower frequencies, which are typically of the order of 100 kilohertz (kHz). To counteract the loss of efficiency, and also to compensate for the problem of current distribution described above, the IRE generator is configured to generate pulses having an amplitude in a range of 1 to 3 kilovolt (kV), and typically about 2 kV, and is able to deliver currents in a range of 15 to 45 Amps, and typically about 30 Amps. The voltage and current of the pulse trains may depend on the impedance between the electrode(s) and patch(es), for example, based on the size of the electrode(s) and patch(es) and distance between the electrode(s) and patch(es).

Each of the pulse trains may have any suitable length, with each of the pulse trains having the same length or different lengths. For example, a pulse train may have a length in a range of 20 to 100 microseconds with a delay between pulse trains in a range of 0.5 milliseconds to 1 second. The delay between the pulse trains may be fixed or variable.

The pulse trains may be monophasic or biphasic and have any suitable duty cycle. In some embodiments, there may be a gap between adjacent pulses. For example, the positive pulse may have a length equal to 50 percent of a period (of a waveform in the trains), the negative pulse may have a length equal to 40 percent of the period, while the gap after each pulse may be equal to 5 percent of the period. In some embodiments, there may be no gap between adjacent pulses. The positive pulses and negative pulses may have the same absolute amplitude or different absolute amplitudes. The pulses may have any suitable shape, for example, square, triangular, trapezoidal, or sine wave.

Unipolar IRE may also be used with multielectrode catheters for example to perform multiple simultaneous ablations, e.g., along a line. Unipolar IRE, whether using a focal catheter or one or more electrodes of a multielectrode catheter, may provide a deeper ablation lesion than bipolar IRE as the pulse trains in unipolar IRE are applied through the tissue from the body part to the skin surface of the patient.

The size and/or number of electrodes and/or body-surface patches may affect the IRE ablation process. If the body-surface patch is (or patches are) too small, the current from the electrical pulse trains may be too concentrated on the skin area leading to damage (e.g., heat damage) of the skin as well as leading to a weak current density at the tissue of the body part which results in poor ablation. Therefore, large patches (e.g., standard patches used for RF ablation) are generally more desirable for unipolar IRE to prevent skin damage as well as to provide a higher concentration of current density at the tissue of the body part. However, larger patches may lead to stimulating muscles too much. Muscle stimulation is generally not a problem with RF ablation which uses lower power and a continuous signal. However, higher power pulse trains may lead to muscle stimulation depending on the size and location of the body-surface patches.

Embodiments of the present invention solve the above problems by allowing one or more different electrodes of a multielectrode catheter (e.g., a balloon or lasso-shape catheter) to be selected by the physician, and one or more body-surface patches to be selected (by the physician or automatically) as the return electrode(s) in order to find a combination of electrodes and patches that keep muscle stimulation within acceptable limits. In some embodiments, the ablation electrode may be part of a focal catheter including a single ablation electrode.

In some embodiments, the body-surface patches may be selected so as to minimize muscle stimulation. For example, one or two patches closest to the catheter or around the catheter (e.g., symmetrically around the body on the chest and back) may be selected and a test pulse train is (or trains are) applied between the catheter electrode(s) and the selected body-surface patches. Movement of the body (e.g., chest or leg) may then be measured to provide a measure of muscle stimulation. If the movement is within a given threshold, the selected body-surface patches are used for future ablations until the movement exceeds the given threshold. If the movement exceeds the given threshold, different or more body-surface patches are selected, e.g., randomly or according to a protocol. Another test pulse train is (or trains are) applied, and the resulting body movement is measured. If the movement exceeds the given threshold, different or more body-surface patches are selected, e.g., randomly or according to the protocol, etc.

The test pulse trains may be applied, and the body movement measured pre-treatment and/or during treatment (e.g., between ablations or even between pulse trains of the same ablation location) as the body movement may depend on proximity of the catheter and/or patches to nerves etc.

System Description

Figure 2:
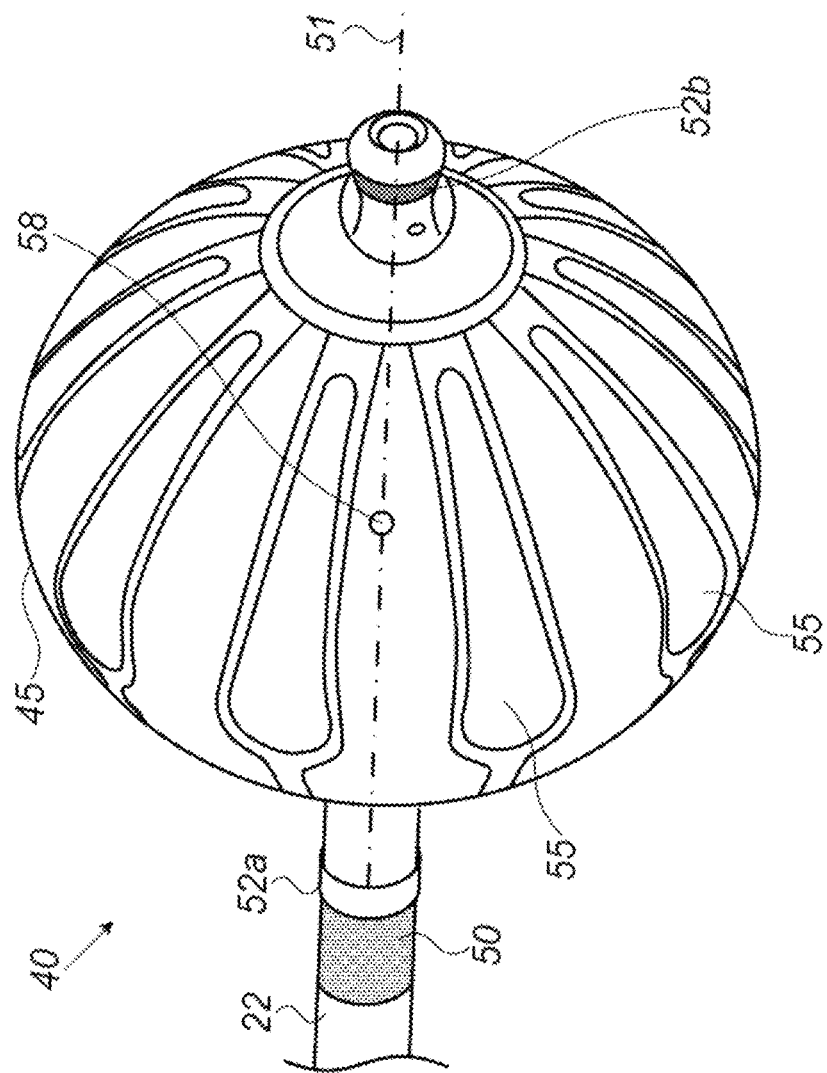

Reference is now made to FIG. 1, which is a schematic pictorial illustration of a catheter-based position tracking and ablation system 20 in accordance with an exemplary embodiment of the present invention. Reference is also made to FIG. 2, which is a schematic pictorial illustration of a balloon catheter 40, in accordance with an embodiment of the present invention.

The position tracking and ablation system 20 is used to determine the position of the balloon catheter 40, seen in an inset 25 of FIG. 1 and in more detail in FIG. 2. The balloon catheter 40 includes a shaft 22 and an inflatable balloon 45 fitted at a distal end of the shaft 22. Typically, the balloon catheter 40 is used for therapeutic treatment, such as spatially ablating cardiac tissue, for example at the left atrium. The catheter 40 is configured to be inserted in a chamber of a heart 26 of a living subject (e.g., a patient 28).

The position tracking and ablation system 20 can determine a position and orientation of the shaft 22 of the balloon catheter 40 based on sensing-electrodes 52 (proximal-electrode 52a and distal-electrode 52b) fitted on the shaft 22, on either side of the inflatable balloon 45 and a magnetic sensor 50 fitted just proximally to proximal-electrode 52a. The proximal-electrode 52a, the distal-electrode 52b, and the magnetic sensor 50 are connected by wires running through the shaft 22 to various driver circuitries in a console 24. In some embodiments, the distal electrode 52*b* may be omitted. The magnetic sensor 50 may comprise a single axis sensor (SAS), or a double axis sensor (DAS), or a triple axis sensor (TAS), by way of example.

The shaft 22 defines a longitudinal axis 51 (FIG. 2). A center-point 58 (FIG. 2) on the axis 51, which is the origin of the sphere shape of the inflatable balloon 45, defines a nominal position of the inflatable balloon 45. Multiple ablation electrodes 55 (only some labeled for the sake of simplicity) are disposed in a circumference over the inflatable balloon 45, which occupy a large area as compared with sensing-electrodes 52*a* and 52*b*. Radio frequency power or IRE ablation signals may be supplied to the ablation electrodes 55 to ablate the cardiac tissue.

Typically, the disposed ablation electrodes 55 are evenly distributed along an equator of the inflatable balloon 45, where the equator is generally aligned perpendicular to the longitudinal axis 51 of the distal end of the shaft 22.

The illustration shown in FIG. 2 is chosen purely for the sake of conceptual clarity. Other configurations of sensing-electrodes 52 and ablation electrodes 55 are possible. Additional functionalities may be included in the magnetic sensor 50. Elements which are not relevant to the disclosed embodiments of the invention, such as irrigation ports, are omitted for the sake of clarity.

A physician 30 navigates the balloon catheter 40 to a target location in the heart 26 of the patient 28 by manipulating the shaft 22 using a manipulator 32 near the proximal end of the catheter and/or deflection from a sheath 23. The balloon catheter 40 is inserted, while the inflatable balloon 45 is deflated, through the sheath 23, and only after the balloon catheter 40 is retracted from the sheath 23 is the inflatable balloon 45 inflated and regains its intended functional shape. By containing balloon catheter 40 in a deflated configuration, the sheath 23 also serves to minimize vascular trauma on its way to the target location.

Console 24 comprises a processor 41, typically a general-purpose computer and a suitable front end and interface circuits 44 for generating signals in, and/or receiving signals from, body-surface patches 49 which are attached by wires running through a cable 39 and configured to be attached to the chest and to the back of the patient 62. In some embodiments, the body-surface patches 49 provide position signals, as described in more detail below. The body-surface patches 49 may comprise respective electrodes 75, and/or respective magnetic sensors 77. Each magnetic sensor 77 may comprise a single axis sensor (SAS), or a double axis sensor (DAS), or a triple axis sensor (TAS), by way of example.

Console 24 further comprises a magnetic-sensing subsystem. The patient 62 is placed in a magnetic field generated by a pad containing magnetic field generator coils 42, which are driven by a unit 43 disposed in the console 24. The magnetic field generator coils 42 are configured to generate alternating magnetic fields is a region including the magnetic sensor 50 and the body-surface patches 49. The magnetic fields generated by the coils 42 generate direction signals in the magnetic sensor 50 and the magnetic sensors 77, which are then provided as corresponding electrical inputs to the processor 41.

In some embodiments, the processor 41 uses the position-signals received from the sensing-electrodes 52, the magnetic sensor 50 and the ablation electrodes 55 to estimate a position of the balloon catheter 40 inside an organ, such as inside a cardiac chamber. In some embodiments, the processor 41 correlates the position signals received from the electrodes 52, 55 with previously acquired magnetic location-calibrated position signals, to estimate the position of the balloon catheter 40 inside a cardiac chamber. The position coordinates of the sensing-electrodes 52 and the ablation electrodes 55 may be determined by the processor 41 based on, among other inputs, measured impedances, or on proportions of currents distribution, between the electrodes 52, 55 and the body-surface patches 49. The console 24 drives a display 27, which shows the distal end of the catheter position inside the heart 26.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in US Patent Publication Nos. 2002/0065455 A1, 2003/0120150 A1 and 2004/0068178 A1.

The Carto®3 system applies an Active Current Location (ACL) impedance-based position-tracking method. In some embodiments, using the above noted ACL method, the processor 41 estimates the positions of the sensing-electrodes 52 and the ablation electrodes 55. In some embodiments, the signals received from the electrodes 52, 55 and/or the body-surface patches 49 are correlated with a matrix which maps impedance (or another electrical value) measured by the sensing-electrodes 52, 55 and/or the body-surface patches 49 with a position that was previously acquired from magnetic location-calibrated position signals.

In some embodiments, to visualize catheters which do not include a magnetic sensor, the processor 41 may apply an electrical signal-based method, referred to as the Independent Current Location (ICL) method. In the ICL method, the processor 41 calculates a local scaling factor for each voxel of a volume of the balloon catheter 40. The factor is determined using a catheter with multiple electrodes having a known spatial relationship, such as a Lasso-shaped catheter. However, although yielding accurate local scaling (e.g., over several millimeters), ICL may be less accurate when applied to a balloon catheter, whose size is on the order of centimeters. In some embodiments, the processor 41 may apply the disclosed ICL method to scale the balloon catheter shape into a correct one, based on known smaller scale distances between electrodes of a lasso-shaped catheter, as well as based on larger scale distances, themselves based on the known distance between the sensing-electrodes 52 at the ends of the inflatable balloon 45.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The medical system 20 may also include an ablation power generator 69 (such as an RF or IRE signal generator) configured to be connected to the catheter 40, and apply an electrical signal (or pulsed trains) between one or more of the electrodes 55 and one or more of the body-surface patches 49 to ablate tissue in the chamber of the heart.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description.

A balloon catheter is described herein by way of example only. The system 20 may be implemented using any suitable electrode catheter or probe having a distal end and one or more ablation electrodes disposed on the distal end, for example, a lasso catheter, a basket catheter, a grid catheter, or a focal catheter including a single ablation electrode.

Figure 3:
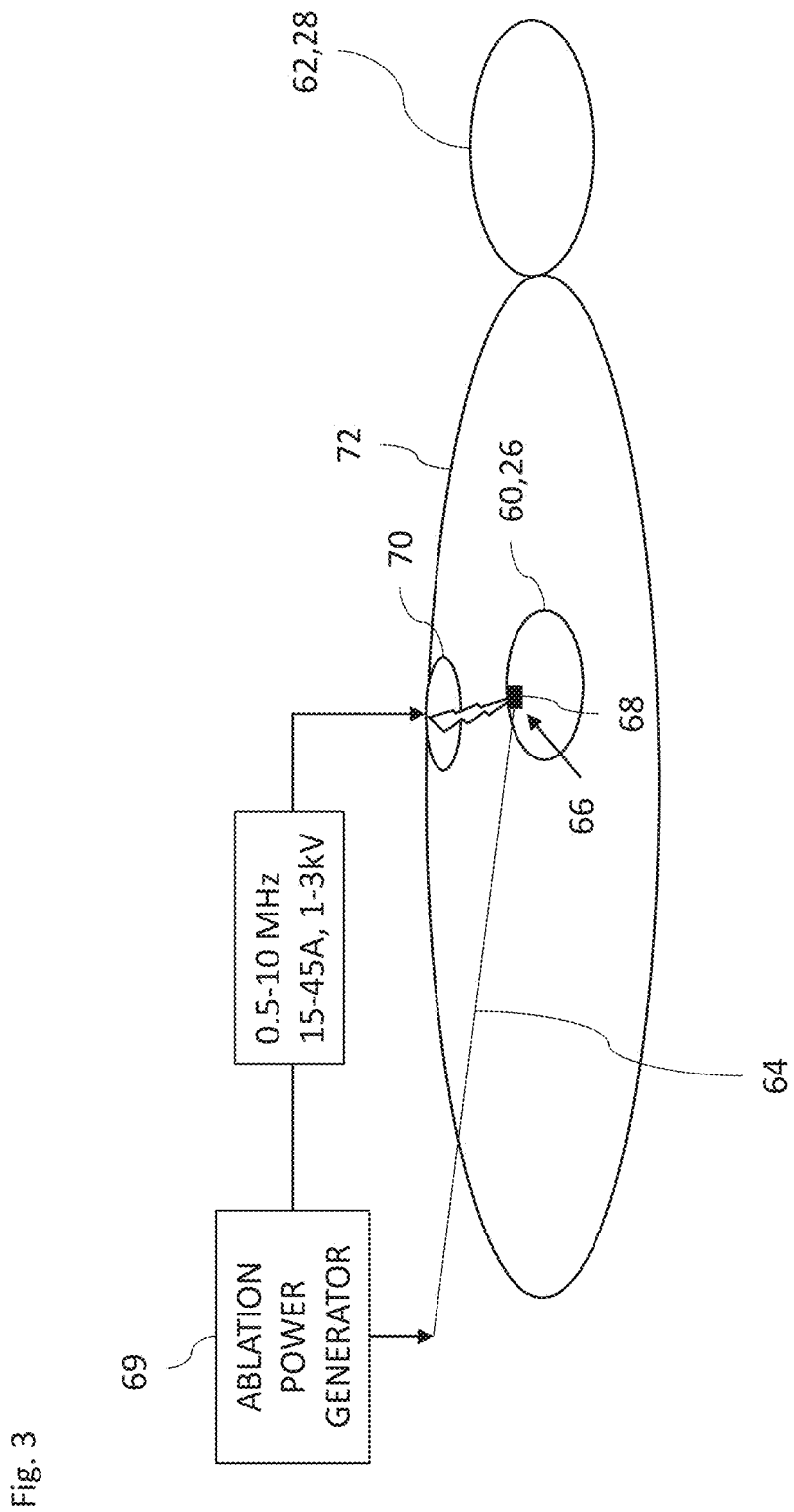

Reference is now made to FIG. 3, which is a schematic view of a body part 60 (e.g., the heart 26) of a living subject 62 (e.g., the patient 2862) being ablated using unipolar electroporation in the system 20 of FIG. 1.

FIG. 3 shows a probe 64 (e.g., the balloon catheter 40) including a distal end 66 including one or more electrodes 68 inserted into the body part 60 of the living subject 62 and one or more body-surface patches 70 (only one shown for the sake of simplicity) configured to be applied to a skin surface 72 of the living subject 62. The ablation power generator 69 is configured to be electrically connected to the electrode(s) 68 and the body-surface patch(es) 70. The ablation power generator 69 is configured to generate multiple electrical pulse trains having a pulse frequency of at least 0.5 megahertz, with respective delays between the electrical pulse trains. The ablation power generator 69 is configured to apply the electrical pulse trains (having the pulse frequency of at least 0.5 megahertz) between the electrode(s) 68 and the body-surface patch(es) 70 so as to electroporate tissue of the body part 60.

In some embodiments, the electrical pulse trains have a pulse frequency of about 1 megahertz. In other embodiments, the electrical pulse trains have a pulse frequency in a range between 0.5 and 10 megahertz. In some embodiments, the electrical pulse trains have a current of about 30 Amps. In other embodiments, the electrical pulse trains have a current in a range between 15 and 45 Amps. In some embodiments, the electrical pulse trains have a voltage of about 2 kilovolts. In other embodiments, the electrical pulse trains have a voltage in a range between 1 and 3 kilovolts.

Each of the pulse trains may have any suitable length, with each of the pulse trains having the same length or different lengths. The delay between the pulse trains may be fixed or variable. In some embodiments, each (or some) of the electrical pulse trains have a length in a range between 20 and 100 microseconds, with each of the respective delays having a length in a range between 0.5 milliseconds and 1 second.

The pulse trains may be monophasic or biphasic and have any suitable duty cycle. In some embodiments, there may be a gap between adjacent pulses. For example, the positive pulse may have a length equal to 50 percent of a period (of a waveform in the trains), the negative pulse may have a length equal to 40 percent of the period, while the gap after each pulse may be equal to 5 percent of the period. In some embodiments, there may be no gap between adjacent pulses. The positive pulses and negative pulses may have the same absolute amplitude or different absolute amplitudes. The pulses may have any suitable shape, for example, square, triangular, trapezoidal, or sine wave.

Figure 4:
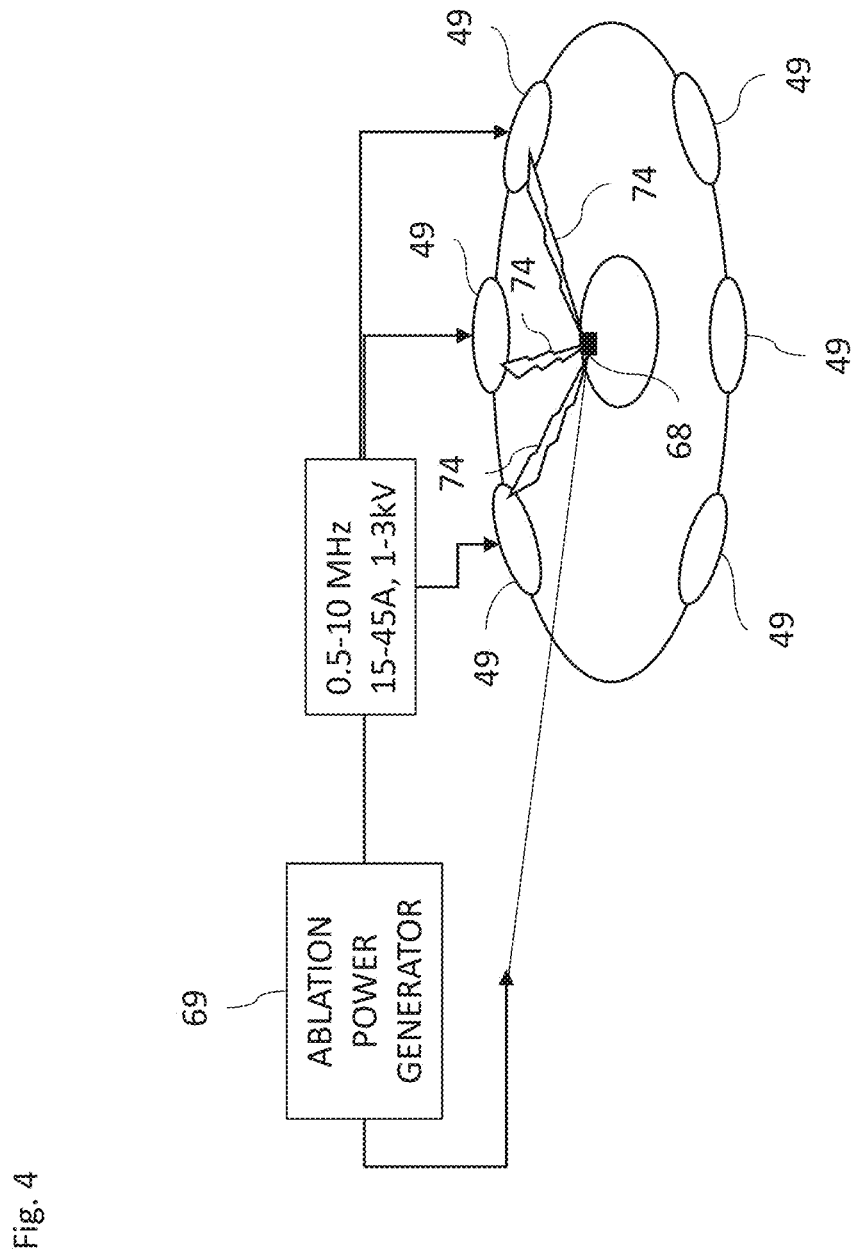

Reference is now made to FIG. 4, which is a schematic view illustrating selectively selecting body-surface patches 49 for use in electroporation in the system 20 of FIG. 1. The physician 30 (FIG. 1) may select one or more of the electrodes 68 for performing IRE ablation. Multiple electrodes 68 may be selected to perform a line ablation. The ablation power generator 69 is configured to be selectively electrically connected to one or more of the electrodes 68 and one or more of the body-surface patches 49. FIG. 4 shows that pulse trains 74 are applied between the selected electrode(s) 68 and three upper body-surface patches 49.

Reference is now made to FIG. 5, which is a flowchart 100 including a method of operation of the system 20 of FIG. 1.

The processor 41 is configured to receive (block 102) a user input (e.g., from the physician 30) setting a movement threshold to determine if a present selection of body-surface patches 49 leads to too much muscle stimulation in response to applied pulse trains, described in more detail below. In some embodiments, a default movement threshold is used unless overridden by the physician 30.

The processor 41 is configured to select (block 104) one or more of the body-surface patches 49. In some embodiments, the initial selected body-surface patches 49 may be selected by the body-surface patches 49 or according to a default sub-set of the body-surface patches 49, or according to a position of the electrodes 68 selected for performing IRE ablation. For example, one or two body-surface patches 49 closest to the probe 64 or around the probe 64 (e.g., symmetrically placed around the body on the chest and back) may be selected. In some embodiments, the selected body-surface patches 49 may include at least one of the body-surface patches 49 attached to a chest of the living subject 62, and at least one of the body-surface patches 49 attached to a back of the living subject 62.

The ablation power generator 69 is configured to generate (block 106) one or more electrical pulse train, and apply the electrical pulse train(s) between the electrode(s) 68 (selected by the physician 30) and the selected body-surface patches 49.

The processor 41 is configured to provide (block 108) a measurement of movement (representative of distance, velocity, and/or acceleration) of the living subject 62 responsively to applying the electrical pulse train(s) between the electrode(s) 68 (selected by the physician 30) and the selected body-surface patches 49. The measurement of movement of the living subject 62 may be a measurement of chest movement or leg movement, for example, of the living subject 62.

In some embodiments, one or more of the body-surface patches 49 are configured to provide one or more position signals. The processor 41 is configured to provide the measurement of movement responsively to the position signal(s). In some embodiments, the processor 41 is configured to compute the measurement of movement responsively to a measurement of displacement, and/or velocity, and/or acceleration of the chest movement responsively to one or more of the position signals. The velocity and acceleration may be computed based on analyzing the movement of the positions of the body-surface patches 49 over time. Alternatively, or additionally, the magnetic sensors 77 may provide signals indicative of acceleration of the body-surface patches 49.

In some embodiments, the magnetic sensors 77 of the body-surface patches 49 are configured to provide respective position signals responsively to sensing the generated alternating magnetic fields generated by the magnetic field generator coils 42. The processor 41 may be configured to compute the measurement of movement responsively to one or more of the position signals received from the magnetic sensors 77.

In some embodiments, one or more of the position signals from the magnetic sensors 77 may be processed to compute the position(s) of the corresponding body-surface patch(es) 49. The computed position(s) may then be used to compute the measurement of movement. For example, the computed positions may be summed, averaged or otherwise combined to compute the measurement of movement. The positions may be relative positions, for example, relative to an origin of a magnetic coordinate system, relative to an average position of the chest or diaphragm, or relative to some other given position. In the above computation, the position of the body-surface patch 49 closest to the diaphragm on the chest may be used. In some embodiments, the positions of a sub-set of the body-surface patches 49 closest to the diaphragm or other position on the chest or body may be used to compute the measurement of movement. In some embodiments, the computation may weight the computed positions of the (subset of) body-surface patches 49 according to the proximity of the corresponding body-surface patches 49 to the diaphragm or other position of the chest or body providing a higher weight to patches 49 that are closer to the diaphragm other position of the chest or body.

In some embodiments, the respective electrodes 75 of the body-surface patches 49 are configured to provide respective position signals. The electrodes 75 may detect signals provided by the catheter electrode(s) 52, 55, 68 and/or from other one or ones of the body-surface patches 49, and/or from a reference electrode (not shown) placed in the heart 26 or on the back of the patient 28, for example. The processor 41 may be configured to compute the measurement of movement responsively to one or more of the position signals received from the electrodes 75. In some embodiments, the processor 41 may be configured to compute the measurement of movement responsively to one of the position signals received from one of the electrodes.

In some embodiments, the position signals from the electrodes 75 may then be used to compute positions of one or more of the body-surface patches 49. One or more of the computed positions may then be used to compute the measurement of movement as described above with reference to the positions computed for the magnetic sensors 77.

In some embodiments, a distribution of current or impedance values over the body-surface patch electrodes 49 may provide an indication of the measurement of movement. Therefore, the measurement of movement may be computed based on the distribution of the current or impedance values of all, or a subset of, the body-surface patch electrodes 49.

The processor 41 is configured to check at decision block 110 if the measurement of movement exceeds the movement threshold. If the measurement of movement does not exceed the threshold (branch 112), the steps of blocks 106 and 108 are repeated. In other words, if an ablation has been initiated or confirmed by the physician 30, that ablation will continue with the same selection of body-surface patches 49 and movement of the patient 62 is intermittently checked. For example, the physician 30 may initiate an ablation including multiple pulse trains during which movement of the patient 2862 is checked intermittently. If the measurement of movement does exceed the threshold (branch 114), the processor 41 is configured select (block 116) new ones of the body-surface patches 49 responsively to the measurement of movement of the living subject exceeding the threshold. The newly selected body-surface patches 49 are connected to the ablation power generator 69 and the steps of blocks 106-110 are repeated. In other words, if an ablation has been initiated or confirmed by the physician 30, that ablation will continue with the newly selected body-surface patches 49 and movement of the patient 2862 is intermittently checked. If ablation was not initiated, a new test pulse train is (or trains are) applied between the selected electrode(s) 68 and the newly selected body-surface patches 49 and movement of the patient 2862 is checked again. Therefore, the ablation power generator 69 is configured to generate one or more additional electrical pulse trains, and apply the additional electrical pulse train(s) between the selected electrode(s) 68 and the newly selected body-surface patches 49.

In some embodiments, the processor 41 is configured to select the newly selected body-surface patches 49 to include the previously selected body-surface patches 49 plus one or more additional ones of the body-surface patches 49. In some embodiments, the processor 41 is configured to randomly select the newly selected body-surface patches 49. In some embodiments, the processor 41 is configured to select the newly selected body-surface patches 49 such that the newly selected body-surface patches 49 are at least partially different to the previously selected body-surface patches 49.

The electrical pulse trains described above may be applied as test pulse trains pre-treatment and/or as real time ablation pulse trains during treatment (e.g., between ablations or even between trains of the same ablation location) as the body movement may depend on proximity of the probe 64 and/or body-surface patches 49 to nerves etc.

When new body-surface patches 49 are selected between pulse trains (e.g., first pulse train(s) and second pulse train(s)) of the same ablation, the processor 41 is configured to select the new body-surface patches 49 while a given ablation location of the body part is being ablated so that the ablation power generator 69 is configured to generate the first electrical pulse train(s) and the second electrical pulse train(s) to ablate the given ablation location of the tissue of the body part.

When new body-surface patches 49 are selected between ablations, the ablation power generator 69 is configured to generate the first electrical pulse train(s) to ablate a first ablation location of tissue of the body part 60 and generate the second electrical pulse(s) train to ablate a second, different, ablation location of the tissue of the body part 60.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:
1. An electroporation ablation system, comprising:
a probe configured to be inserted into a body part of a living subject, and comprising a distal end including at least one electrode;
a plurality of body-surface patches configured to be applied to a skin surface of the living subject;

an ablation power generator configured to be selectively electrically connected to the at least one electrode and at least one of the plurality of body-surface patches, and configured to generate at least one first electrical pulse train, and apply the at least one first electrical pulse train between the at least one electrode and at least a first one of the plurality of body-surface patches; and a processor configured to:
- provide a measurement of movement of the living subject responsively to applying the at least one first electrical pulse train between the at least one electrode and the at least first one of the body-surface patches;
- compare the measurement to a threshold; and
- select at least a second one of the plurality of body-surface patches responsively to the measurement of movement of the living subject exceeding the threshold, and wherein the ablation power generator is configured to generate at least one second electrical pulse train, and apply the at least one second electrical pulse train between the at least one electrode and the at least second one of the plurality of body-surface patches.

2. The system according to claim 1, wherein:
at least a third one of the plurality of body-surface patches is configured to provide at least one position signal; and
the processor is configured to provide the measurement of movement responsively to the at least one position signal.

3. The system according to claim 2, further comprising magnetic field generator coils configured to generate alternating magnetic fields in a region including the at least third one of the plurality of body-surface patches, wherein:
the at least third one of the plurality of body-surface patches comprises at least one magnetic sensor configured to provide the at least one position signal responsively to sensing the generated alternating magnetic fields; and
the processor is configured to compute the measurement of movement responsively to the at least one position signal received from the at least one magnetic sensor.

4. The system according to claim 2, wherein:
the at least third one of the plurality of body-surface patches comprises at least one respective patch electrode configured to provide the at least one position signal; and
the processor is configured to compute the measurement of movement responsively to the at least one position signal received from the at least one respective patch electrode.

5. The system according to claim 1, wherein:
the processor is configured to select the at least second one of the plurality of body-surface patches while a given ablation location of the body part is being ablated; and
the ablation power generator is configured to generate the at least one first electrical pulse train and the at least one second electrical pulse train to ablate the given ablation location of the body part.

6. The system according to claim 1, wherein the ablation power generator is configured to generate: the at least one first electrical pulse train to ablate a first ablation location of the body part; and the at least one second electrical pulse train to ablate a second, different, ablation location of the body part.

7. The system according to claim 1, wherein the processor is configured to select two of the plurality of body-surface patches such that the two include the at least first one of the plurality of body-surface patches and at least another one of the plurality of body-surface patches.

8. The system according to claim 1, wherein the at least second one of the plurality of body-surface patches includes a sub-set of the plurality of body-surface patches and wherein the processor is configured to randomly select at least one of the sub-set of the plurality of body-surface patches.

9. The system according to claim 1, wherein the at least first one of the plurality of body-surface patches includes a first sub-set of the plurality of body-surface patches and the at least second one includes a second sub-set of the plurality of body-surface patches and wherein the first sub-set of the plurality of body-surface patches is other than the second-sub groupsub-set of the plurality of body-surface patches.

10. The system according to claim 1, wherein the at least first one of the plurality of body-surface patches includes a first body-surface patch configured to be attached to a chest of the living subject, and a second body-surface patch configured to be attached to a back of the living subject.

11. An electroporation ablation method, comprising:
generating at least one first electrical pulse train;
applying the at least one first electrical pulse train between: at least one electrode of a distal end of a probe inserted into a body part of a living subject; and at least a first one of a plurality of body-surface patches applied to a skin surface of the living subject;
providing a measurement of movement of the living subject responsively to applying the at least one first electrical pulse train between the at least one electrode and the at least first one of the body-surface patches;
comparing the measurement to a threshold;
selecting at least a second one of the plurality of the body-surface patches responsively to the measurement of movement of the living subject exceeding the threshold;
generating at least one second electrical pulse train; and
applying the at least one second electrical pulse train between the at least one electrode and the at least second one of the plurality of body-surface patches.

12. The method according to claim 11, wherein:
at least a third one of the plurality of body-surface patches is configured to provide at least one position signal; and
the providing includes providing the measurement of movement responsively to the at least one position signal.

13. The method according to claim 12, further comprising:
generating alternating magnetic fields in a region including the at least third one of the plurality of body-surface patches;
at least one magnetic sensor comprised in the at least third one of the body-surface patches providing the at least one position signal responsively to sensing the generated alternating magnetic fields; and
computing the measurement of movement responsively to the at least one position signal received from the at least one magnetic sensor.

14. The method according to claim 12, further comprising:
providing the at least one position signal by at least one respective patch electrode comprised in the at least third one of the plurality of body-surface patches; and
computing the measurement of movement responsively to the at least one position signal received from the at least one respective patch electrode.

15. The method according to claim 11, further comprising:
   selecting the at least second one of the plurality of body-surface patches while a given ablation location of the body part is being ablated; and
   generating the at least one first electrical pulse train and the at least one second electrical pulse train to ablate the given ablation location of the body part.

16. The method according to claim 11, wherein: the generating of the at least one first electrical pulse train is performed to ablate a first ablation location of the body part; and the generating of the at least one second electrical pulse train is performed to ablate a second, different, ablation location of the body part.

17. The method according to claim 11, wherein the selecting of the at least second one of the plurality of body-surface patches is performed such that the at least second one of the plurality of body-surface patches includes the at least first one of the plurality of body-surface patches and at least another one of the plurality of the body-surface patches patches.

18. The method according to claim 11, wherein the at least second one of the plurality of body-surface patches includes a sub-set of the plurality of body-surface patches and wherein the selecting includes randomly selecting at least one of the sub-set of the plurality of body-surface patches.

19. The method according to claim 11, wherein the at least first one of the plurality of body-surface patches includes a first sub-set of the plurality of body-surface patches and the at least second one of the plurality of body-surface patches includes a second sub-set of the plurality of body-surface patches and wherein the selecting of the at least second one of the plurality of body-surface patches is performed such that the second sub-set of the plurality of body-surface patches is other than the first sub-set of the plurality of body-surface patches.

20. The method according to claim 11, further comprising selecting the at least first one of the plurality of body-surface patches to include at least one of the plurality of body-surface patches configured to be attached to a chest of the living subject, and at least one of the plurality of body-surface patches configured to be attached to a back of the living subject.

* * * * *